US012782270B2

(12) United States Patent
Staubmann et al.

(10) Patent No.: US 12,782,270 B2
(45) Date of Patent: Nov. 3, 2026

(54) METHOD AND DEVICE FOR DETERMINING WHETHER AN OILSEED, A NUT, IN PARTICULAR A HAZELNUT, OR A SEED IS RANCID

(71) Applicant: Insort GmbH, Kirchberg an der Raab (AT)

(72) Inventors: Philipp Staubmann, Weiz (AT); Anton Scheibelmasser, Graz (AT)

( * ) Notice: Subject to any disclaimer, the term of this patent is extended or adjusted under 35 U.S.C. 154(b) by 150 days.

(21) Appl. No.: 18/836,554

(22) PCT Filed: Feb. 6, 2023

(86) PCT No.: PCT/IB2023/051033
§ 371 (c)(1),
(2) Date: Aug. 7, 2024

(87) PCT Pub. No.: WO2023/148692
PCT Pub. Date: Aug. 10, 2023

(65) Prior Publication Data

US 2025/0155363 A1 May 15, 2025

(30) Foreign Application Priority Data

Feb. 7, 2022 (AT) .............................. A 50072/2022

(51) Int. Cl.
*G01N 21/31* (2006.01)
*B07C 5/34* (2006.01)
(Continued)

(52) U.S. Cl.
CPC ........... *G01N 21/31* (2013.01); *B07C 5/3416* (2013.01); *G01N 21/94* (2013.01); *G01N 33/025* (2013.01); *G01N 2021/8466* (2013.01)

(58) Field of Classification Search
CPC ...... G01N 21/31; G01N 21/94; G01N 33/025; G01N 2021/8466; G01N 33/02; B07C 5/3416
See application file for complete search history.

(56) References Cited

U.S. PATENT DOCUMENTS

2020/0152312 A1* 5/2020 Connor .................. G06V 20/20
2020/0288982 A1* 9/2020 Islam ..................... A61C 19/04
(Continued)

FOREIGN PATENT DOCUMENTS

CN 113420614 A * 9/2021 ............. G06F 18/24

OTHER PUBLICATIONS

Fukushima, Kunihiko. "Neocognitron: A self-organizing neural network model for a mechanism of pattern recognition unaffected by shift in position." Biological cybernetics 36.4 (1980): 193-202. (Year: 1980).*

*Primary Examiner* — Uzma Alam
*Assistant Examiner* — Richard O Toohey
(74) *Attorney, Agent, or Firm* — Outside General Counsel, LLP; Alexander Franco

(57) ABSTRACT

The invention relates to a method for determining whether an oilseed, a nut, in particular a hazelnut (2), or a seed is rancid, involving irradiating a sample, detecting an absorption or reflection spectrum, determining the content of at least one fatty acid decomposition product in the sample, and ascertaining a degree of rancidity using the content of the at least one fatty acid decomposition product in the sample. The method additionally involves irradiating an oilseed, a nut, in particular a hazelnut (2), or a seed, projecting reflected and/or transmitted light onto a detection photosensor (4'), detecting absorption or reflection spectra in a wavelength range of 300-2500 nm using the detection photosensor (4'), said detection photosensor having a plu-
(Continued)

rality of pixels, and assigning a degree of rancidity to each pixel of the detection photosensor (4').

20 Claims, 3 Drawing Sheets

(51) Int. Cl.

| | |
|---|---|
| ***G01N 21/84*** | (2006.01) |
| ***G01N 21/94*** | (2006.01) |
| ***G01N 33/02*** | (2006.01) |

(56) References Cited

U.S. PATENT DOCUMENTS

2020/0378941 A1* 12/2020 Paltauf .................. G01N 33/03
2021/0140887 A1* 5/2021 Akiyama ............. G01N 33/533
2022/0412884 A1* 12/2022 Martin ................. G06V 10/143

* cited by examiner

METHOD AND DEVICE FOR DETERMINING WHETHER AN OILSEED, A NUT, IN PARTICULAR A HAZELNUT, OR A SEED IS RANCID

The invention relates to a method for determining whether an oily fruit, a nut, in particular a hazelnut, or a seed is putrid, in accordance with the preamble of claim 1.

Furthermore, the invention relates to a device for determining whether an oily fruit, a nut, in particular a hazelnut, or a seed is putrid, in accordance with the preamble of claim 19.

Technological Background

The detection and subsequent sorting of bulk materials with the aid of photosensors is a widely used method which is applied on an industrial scale. In methods of this type which are known in the art, seeds are spectroscopically examined individually by irradiating them with a light source. An absorption or reflection spectrum or reflectivity spectrum is then recorded from a photosensor. A processing unit then analyses the absorption or reflection spectrum of each seed in a range of interest and computes the content of a specific constituent of the seed with the aid of a calibration curve.

The identification of various ingredients in individual elements of a bulk material is of interest, for example, in the food industry so as to be able to distinguish between spoiled elements and unspoiled elements of the bulk material. According to the prior art, such processes usually operate in the near infrared region. In order to enable those processes to be used in production facilities, it is necessary for the photosensors employed to have high refresh rates, as a rule of 500 Hz or more. Thus, it becomes possible to ensure a high throughput, while at the same time reliably analysing the ingredients of each individual element that is examined. Conventionally, data collected by the photosensors are analysed by means of conventional statistical classification methods such as Partial Least Squares, Principal Component Regression or the like. This qualitative analysis produces very good results if there are clear differences between spoiled elements and unspoiled elements in the absorption or reflection spectrum.

Hazelnuts are processed as the whole hazelnut in many products. Hazelnuts which qualitatively appear to be perfect on the outside often have already started to putrefy on the inside. Thus, they cannot be differentiated using conventional optical methods operating in the visible region. There are many causes and they are linked to improper storage, insect infestation or mould formation. Frequently, the putrefaction process is also linked to the hazardous formation of mould (toxins, for example aflatoxin). Mould is formed by a mould fungus: in microbiology, mould fungi are a systemically heterogeneous group of filamentous fungi, most of which belong to the Ascomycetes and Zygomycetes taxonomic groups. Mould fungi such as *Aspergillus flavus* are present in soil, rotting vegetation as well as hay and grain exposed to microbial decomposition. A mould fungus attacks the fruit from the outside and sits on the surface.

Putrefaction is defined in ecology and thanatology as the oxygen-deprived decomposition of biological materials by microorganisms. Frequently, the decomposition is described as putrefaction, with the formation of an unpleasant smell. Putrefaction is a natural form of fermentation and is designated here as putrescence. The occurrence of putrefaction is therefore significantly different from mould. Here, an alteration in flavour and also deleterious health-related effects may occur. In any case, however, putrid hazelnuts, whether raw or roasted, have to be removed from the end product. However, because this is not a case of a yes/no decision, but rather a gradual quality criterion has to be applied, this requires a precise detection and assessment of the putrefaction.

CN 113420614 A is known in the prior art. It discloses a method for identifying mildewed peanuts, in particular a method for identifying mildewed peanuts based on a near-infrared hyperspectral image on the basis of a deep learning algorithm with a neural network. The neural network described therein comprises 265 neurons at the input and two neurons at the output of the neural network. Mention is also made of a characteristic wavelength at 1343 nm which is used to carry out a presegmentation. The mould fungus product aflatoxin is detected in this regard. A distribution map of peanut mildewing information is produced, wherein by means of the number of mildewed pixels at the detector and a threshold value (B), each peanut particle in the distribution map of the mildewed information is recorded in order to identify a mildewed peanut and in order to produce a diagram of the mildewed peanut identification result.

The disadvantage with that known solution is that the mould formation occurs at the surface of the peanut, and therefore only superficial information regarding the peanut is examined. Because of its parameterization when detecting mould on peanuts, the clearly necessary Deep Learning Algorithm which is described in detail may lead to a desired result, but it is not suitable for early detection or putrefaction or putrescence.

AT 519918 A1 or WO 2018/191 768 A1 is known in the prior art. It discloses a method for detecting the rancidity of oily fruit, seeds and nuts. "Rancid" means the state in which fats and other lipids decompose by oxidation or fat-cleaving enzymes (lipases). The spoiling of plant and animal fats which can even be discerned in the early stages thereof by alterations to the smell and flavour (rancidity) is due on the one hand, in the case of fats containing water, to hydrolysis and associated cleavage of long-chain fats, and on the other hand to the action of oxygen in the air (oxidation). That patent application comprises the irradiation of a sample of an oily fruit, a nut or a seed with a source of light and detecting the absorption or reflection spectrum of the reflected or transmitted light. The absorption or reflection spectrum is then compared with an external chemical analysis of the sample in order to generate a link between the absorption or reflection spectrum and a rancidity of the sample.

A disadvantage with known methods in the prior art lies in the fact that only the rancidity of the oily fruit or nut can be determined, and in that as soon as a marker is distinguished in the absorption or reflection spectrum which classifies a product as a bad product, this is immediately ejected. However, when the difference between the spectrum of a good product and a bad product Is very small, then the small difference is greatly magnified in the external process in a manner such that the signal/noise ratio increases greatly and the uncertainty of the decision between a good product and a bad product increases greatly. The differences in the spectrum are additionally determined from good and bad examples with the aid of a reference sample. Because, however, natural products which have a spectral dispersion are involved, this comparison suffers from high uncertainty and can vary with each batch. Contamination or product defects are additionally more often distributed over the product in an irregular manner. The result of an incorrect classification is a defective separation of good and spoiled foodstuffs.

In summary, therefore, conventional determination methods in the foodstuffs industry lead to a large quantity of rejects when processing oily fruit, nuts, in particular hazelnuts, or seeds, whereas at least a portion of these rejected products could still be used or still be processed. At the same time, excessive rejection could also have economical disadvantages.

DESCRIPTION OF THE INVENTION

An objective of the invention is to overcome at least one of the disadvantages of the prior art. In particular, an objective is achieved by providing a method and a device for determining whether an oily fruit, a nut, in particular a hazelnut, or a seed is putrid, in order to reduce rejections in the determination method compared with known procedures. This is particularly critical if products contain substances which can lead to consumers' health being damaged. In any case, a compromise in the quality of the product involves a compromise to the flavour. This is particularly the case when processing hazelnuts.

This objective is achieved by the features of the independent claims. Advantageous further embodiments are defined in the figures and in the dependent patent claims.

The method in accordance with the invention for determining whether an oily fruit, a nut, in particular a hazelnut, or a seed is putrid, comprises at least the calibration steps of:

a) irradiating a sample of an oily fruit, a nut, in particular a hazelnut, or a seed with a calibrating light source,
b) acquiring an absorption or reflection spectrum in a wavelength range of 300-2500 nm by means of a calibrating photosensor,
c) associating at least one characteristic wavelength or at least one characteristic wavelength range of the acquired absorption or reflection spectrum of the sample with a degree of putrescence,
d) repeating the preceding steps for a representative number of samples and forming a correlation between the degree of putrescence and the associated wavelengths or wavelength ranges of the acquired absorption or reflection spectra.

By means of the calibration steps, a correlation between a value for the absorption or reflection spectrum at a characteristic wavelength or in at least one characteristic wavelength range, and the degree of putrescence of the sample is generated. A correlation describes a relationship between two or more features, states or functions, wherein here, a causal correlation is especially recommended.

This means that a determination of the degree of putrescence of the oily fruit, a nut, in particular a hazelnut, or a seed is made possible purely with the aid of an evaluation of the absorption or reflection spectrum, without the need for a separate additional analysis such as a laboratory analysis.

Preferably, the calibration steps are carried out in the aforementioned order in order to enable a reproducible calibration to be made, in particular for hazelnuts.

Furthermore, the method in accordance with the invention comprises the detection steps of:

e) irradiating an oily fruit, a nut, in particular a hazelnut, or a seed with a detecting light source,
f) acquiring absorption or reflection spectra in a wavelength range of 300-2500 nm, by means of a detecting photosensor, wherein the detecting photosensor has a plurality of pixels and each acquires one absorption or reflection spectrum per pixel,
g) associating a degree of putrescence with each pixel of the detecting photosensor by applying the correlation in accordance with step d) to the absorption or reflection spectra acquired from the pixels of the detecting photosensor,
h) classifying the oily fruit, the nut, in particular the hazelnut, or the seed as putrid when at least a specific number of pixels have a degree of putrescence which exceeds a first threshold value and/or when a degree of putrescence associated with at least one pixel exceeds a second threshold value.

The detection steps enable a reproducible evaluation of acquired absorption or reflection spectra to be made with the aid of the calibration steps which have previously been carried out.

Preferably, the detection steps are carried out in the aforementioned order to enable a reproducible detection of putrefaction, in particular for hazelnuts, to be made.

In accordance with the invention, the absorption or reflection spectra are acquired for every individual pixel of the detecting photosensor, and a degree of putrescence is associated with each of these spectra by means of the correlation generated in the calibration steps. This has the advantage that it is not a single absorption or reflection spectrum per irradiated oily fruit, nut, in particular hazelnut, or seed that is called upon for the evaluation in order to decide whether the oily fruit, nut, in particular hazelnut, or seed in question is putrid. Thus, an additional criterion can be introduced, namely that a specific number of pixels must have a degree of putrescence which exceeds a first threshold value. The detecting photosensor here has a plurality of pixels and each one acquires one absorption or reflection spectrum per pixel. The first threshold value is therefore examined for every pixel at the detecting photosensor.

The measured values or the spectra per pixel at the detecting photosensor are defined as the degree of putrescence, for example in a range of 0-100%. Subsequently, with the aid of the first threshold value or the second threshold value, sorting may be carried out, for example in a sorting unit.

As an alternative or in addition to this, the oily fruit, nut or the seed in question may also be eliminated if a degree of putrescence associated with at least one pixel exceeds a second threshold value. By defining the first threshold value and the number of pixels the degree of putrescence of which must exceed this first threshold value, as well as the second threshold value, the method in accordance with the invention enables inhomogeneities in the putrefaction process in the agricultural natural products tested by means of the method in accordance with the invention to be taken into consideration. This means that a substantially more focussed sorting into good products and bad products can be carried out than was previously possible with prior art methods.

The method in accordance with the invention enables the putrescence of the oily fruit, the nut, in particular the hazelnut, or the seed to be determined with the aid of a spatially resolved determination of the degree of putrescence. In addition, by means of the first threshold value and the second threshold value, a non-homogeneous distribution of the fatty acid decomposition products in the oily fruit, the nut, in particular the hazelnut, or the seed can be incorporated into the evaluation of the putrescence. This results in an improved distinction between a hazelnut, for example, which is not putrid and a putrid hazelnut.

Preferably, in step a) and/or in step e). the sample of the oily fruit, the nut, in particular the hazelnut, or the seed moves past the respective light source. This means that the aforementioned method can be applied to moving oily fruit, so that sorting of putrid and good oily fruit in the process is facilitated. With the aid of the aforementioned method, large mass flowrates of oily fruits, such as 6 t/h, for example, can be sorted swiftly.

Preferably, before step b), the light reflected and/or transmitted from the sample is projected onto a calibration photosensor. This means that acquisition of the spectra can be improved.

Preferably, in step b), a wavelength range of 900-1700 nm is used. This means that the infrared region of the light and the associated information can be measured better for the calibration of the degree of putrescence.

Preferably, after step b), a degree of putrescence is determined with the aid of the content of at least one fatty acid decomposition product in the sample. This means that fatty acid decomposition products are searched for in the spectral range employed, in order to provide a reproducible detection of putrid oily fruit.

In particular, after step b), a degree of putrescence is determined with the aid of the content of at least one fatty acid decomposition product in the sample and additionally with the aid of the content of an acetic acid in the sample. Here, the at least one fatty acid decomposition product content and the acetic acid content are mathematically linked in the evaluation, for example by forming a mean, a median or by addition. As an alternative or in addition, a weighting of the contents may be carried out. This will enhance the precision in the classification in the method in accordance with the invention.

Preferably, the at least one fatty acid decomposition product comprises at least one component from the group: butyrolactone, diacetyl, 2-methylbutanal, 3-methylbutanal, acetylacetone, filbertone or 2,3-butanediol. A model may be prepared which is not restricted to one chemical substance, but any component may be used which exhibits a significant difference in concentration between good and putrid oily fruits, nuts, in particular hazelnuts, or seeds. This means that in the decisive spectral range, with the aid of the measured values of a plurality of components or substances which are putrid, a conclusion can automatically be drawn from the relative or the absolute amplitudes in the spectrum regarding the quantitative level of flavour-altering substances. As an example, a normalisation of the values may be carried out and subsequently, the spectra could be differentiated and compared.

Preferably, the degree of putrescence is determined with the aid of the contents of at least two fatty acid decomposition products in the sample. As an example, those two fatty acid decomposition products are included which have the largest difference in concentration between putrid oily fruit and good oily fruit. The contents are mathematically linked in the evaluation, for example by forming a mean, a median or by addition. As an alternative or in addition, a weighting of the contents may be carried out. Since at least two ingredients which are characteristic of the putrefaction process are taken into consideration for determining the degree of putrescence, the accuracy of the method in accordance with the invention is further increased.

Preferably, several components of the fatty acid decomposition products which have the largest difference in concentration between good and putrid oily fruits, nuts, in particular hazelnuts, or seeds are searched for. In this regard, the model is, for example, broken down into five components which exhibit the largest difference in concentrations between spectra for good and putrid oily fruit, nuts, in particular hazelnuts, or seeds. This means that in the crucial spectral region, with the aid of the measured values from a plurality of substances, better conclusions can automatically be drawn from the absolute amplitudes in the spectrum as to the quantitative level of the flavour-altering substances.

Preferably, the correlation is at least one correlation function or at least one index table or a value table, or comprises at least one comparison of spectral information which contains at least the degree of putrescence and the wavelengths or wavelength ranges of the acquired absorption or reflection spectra associated therewith. A correlation may comprise a correlation function, an index table, a value table or the like, so that a causal relationship between the degree of putrescence and the associated wavelengths or wavelength ranges of the acquired absorption or reflection spectra can be formed. A correlation function enables a consistent relationship to be formed between the degree of putrescence and the associated wavelengths or wavelength ranges of the acquired absorption or reflection spectra and therefore enables a complete and accurate causal relationship to be formed. Index tables or even value tables do not in fact comprise any consistent causal relationships between the degree of putrescence and the associated wavelengths or wavelength ranges of the acquired absorption or reflection spectra, however for some oily fruits, this is sufficiently good for reproducible sorting of putrid oily fruit and good oily fruit to be detected.

Preferably, before step e), the light reflected and/or transmitted from the oily fruit, the nut, in particular the hazelnut, or the seed is projected onto a detecting photosensor. This means that the association of the measured values with the degree of putrescence is improved.

Preferably, a wavelength range of 900-1700 nm is used in step e). In this way, the infrared region of the light and the information linked to it for detecting the degree of putrescence can be measured in an improved manner.

In accordance with a preferred embodiment of the method in accordance with the invention, the association of the at least one characteristic wavelength or of the at least one characteristic wavelength range of the acquired absorption or reflection spectrum of the sample with the degree of putrescence is carried out by means of at least one mean or median, a bandwidth or individual frequency bands of the acquired absorption or reflection spectrum. This has the advantage that a focussed correspondence between the acquired absorption or reflection spectrum and the degree of putrescence is produced.

Preferably, the correlation in an operating mode which is characterized by the detection steps is used in order to associate a corresponding measured value or reference value for the degree of putrescence with newly recorded spectra.

Preferably, the determination of the content of the at least one fatty acid decomposition product in the sample comprises carrying out a measurement in the measuring laboratory, namely in particular, gas chromatography and a subsequent mass spectrometric analysis. What is important here is the good separation between good and bad products during the laboratory analysis of the chemical substances, which can be seen very well using a scatter plot for the chemical substances used over the measured samples, for example hazelnut samples. It is a necessary but not sufficient condition for a good quantitative model. Whether a substance can then be used quantitatively with the aid of the NIR spectrum depends on the position of additional chemical substances which are quite capable of masking the absorption bands.

Preferably, a reference value based on the calibration by means of the determined correlation between spectral data and the measuring laboratory corresponds to each pixel. The correlation obtained, i.e. that spectral information which can be associated with the information in the reference data set, is then used in an operating mode which is characterized by the detection steps in order to associate appropriate measured values for the degree of putrescence with freshly recorded spectra.

In accordance with a preferred embodiment of the method in accordance with the invention, a common sensor is used as the calibrating photosensor and as the detecting photosensor. This has the advantage that only a single sensor is necessary for the calibration steps and the detection steps. In addition in this regard, one light source may be used as the calibrating light source and as the detection light source. This has the advantage that only a single light source is necessary for the calibration and the detection steps. This reduces the costs for the application of the method in accordance with the invention.

Preferably, the acquisition of the absorption or reflection spectra is carried out by the calibrating photosensor and/or the detecting photosensor by means of hyperspectral acquisition. This means that a particularly large wavelength range can be measured. Preferably, hyperspectral cameras are used in this regard. In particular, the acquisition of the absorption or reflection spectra is carried out by the calibrating photosensor and/or the detecting photosensor by means of a colour camera. This means that an additional range of 380-780 nm can be acquired. As an example, discoloured oily fruit are detected with the colour camera and can easily be rejected. In addition to putrid oily fruit, discoloured oily fruit can also be rejected, so that the quality of sorting is improved. Discolorations could also indicate other unwanted reductions in quality in oily fruit. Particularly preferably, the measured information from the colour camera is evaluated with the AI module which will be described below. This means that the desired detection rate can be raised to 99%.

In accordance with the preferred embodiment of the method in accordance with the invention, the determination of the content of the at least one fatty acid decomposition product in the sample comprises carrying out gas chromatography and a subsequent mass spectrometric analysis. This means that a particularly accurate determination of the fatty acid decomposition product content can be obtained.

The device in accordance with the invention for determining whether an oily fruit, a nut, in particular a hazelnut, or a seed is putrid, comprises a calibrating light source, a detecting light source, a calibrating photosensor and a detecting photosensor and is configured to carry out at least one method in accordance with the invention disclosed herein.

Preferably, the device comprises a sorting unit, wherein the sorting unit is configured to reject an oily fruit, a nut, in particular a hazelnut, or a seed from a product stream when the oily fruit, the nut, in particular the hazelnut, or the seed is classified as putrid. This has the advantage that the method in accordance with the invention can be used on an industrial scale.

A preferred embodiment of the aforementioned method for determining whether an oily fruit, a nut, in particular a hazelnut, or a seed is putrid, comprises the calibration steps of:

irradiating a sample of an oily fruit, a nut, in particular a hazelnut, or a seed with a calibrating light source, projecting the light reflected and/or transmitted from the sample onto a calibrating photosensor (4), acquiring an absorption or reflection spectrum in a wavelength range of 300-2500 nm, preferably 900-1700 nm, via the calibrating photosensor, determining a content of at least one fatty acid decomposition product in the sample, determining a degree of putrescence with the aid of the content of the at least one fatty acid decomposition product in the sample, associating at least one characteristic wavelength or at least one characteristic wavelength range of the acquired absorption or reflection spectra of the sample with the degree of putrescence, repeating the preceding steps for a representative number of samples and forming a correlation function between the degree of putrescence and the associated wavelengths or wavelength ranges of the acquired absorption or reflection spectra, characterized in that the method comprises the detection steps of irradiating an oily fruit, a nut, in particular a hazelnut, or a seed with a detecting light source, projecting the light reflected and/or transmitted by the oily fruit, the nut, in particular the hazelnut, or the seed onto a detecting photosensor, acquiring absorption or reflection spectra in a wavelength range of 300-2500 nm, preferably 900-1700 nm, by means of the detecting photosensor, wherein the detecting photosensor has a plurality of pixels and each acquires one absorption or reflection spectrum per pixel, associating a degree of putrescence with each pixel of the detecting photosensor by applying the correlation function to the absorption or reflection spectra acquired from the pixels of the detecting photosensor, classifying the oily fruit, the nut, in particular the hazelnut, or the seed as putrid when at least a specific number of pixels have a degree of putrescence which exceeds a first threshold value and/or when a degree of putrescence associated with at least one pixel exceeds a second threshold value.

In this regard, a common sensor may be used as the calibrating photosensor and as the detecting photosensor.

Furthermore, one light source may be used as the calibrating light source and as the detecting light source.

In particular, the degree of putrescence is determined with the aid of the contents of at least two fatty acid decomposition products in the sample.

In particular, the association of the at least one characterizing wavelength or of the at least one characterizing wavelength range of the acquired absorption or reflection spectrum of the sample with the degree of putrescence is carried out by means of at least a mean, a bandwidth or individual frequency bands of the acquired absorption or reflection spectra.

Preferably, the acquisition of the absorption or reflection spectrum is carried out via the calibrating photosensor and/or the detecting photosensor by means of hyperspectral acquisition.

In particular, the determination of the content of the at least one fatty acid decomposition product in the sample comprises carrying out a gas chromatography and a subsequent mass spectrometric analysis.

A preferred embodiment of the device for determining whether an oily fruit, a nut, in particular a hazelnut, or a seed is putrid comprises a calibrating light source, a detecting light source, a calibrating photosensor and a detecting photosensor, and is configured for carrying out one of the aforementioned methods.

Preferably, the device comprises a sorting unit, wherein the sorting unit is configured to reject an oily fruit, a nut, in particular a hazelnut, or a seed from a product stream when the oily fruit, the nut, in particular the hazelnut, or the seed is classified as putrid.

Preferably, the device comprises a control device. The control device may control at least one component from the group: calibrating photosensor, detecting photosensor, calibrating light source and detecting light source, so that at least one method as described above can proceed in an automatic and reproducible manner. In particular, the control device enables an output device to output at least one measured value. A display is provided, for example, as the output device, on which at least one piece of indicative information for the putrescence of the oily fruit is output. As an example, a distribution function or statistical data for the putrid oily fruit present in the product stream or mass flow is output. This means that process monitoring is improved.

In particular, the control device controls the sorting unit. In this regard, the control device has control data which control the sorting unit. As an example, the sorting unit may comprise a pneumatic deflecting unit which is connected to the detecting photosensor. With the aid of the control data, the pneumatic deflecting unit separates the oily fruit, nuts, in particular hazelnuts, or seeds classified as putrid from a substantially continuous product stream. In this regard, as an example, the strength and in particular the direction, of the compressed air of the pneumatic deflecting unit may be controlled.

Preferably, the sorting unit operates with at least two adjustable threshold values, wherein a first adjustable threshold value comprises a quantity of substance for a pixel and the second adjustable threshold value comprises a non-homogeneous distribution of the substance, wherein for sorting, the second adjustable threshold value takes into consideration the number of pixels with the attribution "putrid".

Preferably, the device comprises a processing unit which evaluates spectral data in order to carry out a classification of the oily fruit. The spectral data may be measured data and may be used to generate control data for the control unit, wherein the control data are subsequently used, in particular in order to control the sorting unit.

In particular, the processing unit is configured to compute at least one of the two threshold values based on the measured data or spectral data and to generate control data for the control device therefrom.

Preferably, an AI (artificial intelligence) module is present which is connected to the processing unit. The aforementioned solution demands specialist knowledge regarding the absorption bands of the oily fruit and of the fatty acid decomposition products in the infrared region in order to select the correct spectral region and therefore to carry out an optimal calibration for the difference between good products and putrid oily fruit. With the aid of Deep Learning Algorithms, along with the assistance of neural networks, the need for this physical chemical specialist knowledge is dispensed with. Historical measured data or spectra from predominantly putrid samples and predominantly good samples can be made available to the neural network as learning data. These neural networks autonomously find the optimal region of interest in the measured data or in the spectra. In this manner, the calibration via the recorded spectral data, in particular the hyperspectral data, is further improved. "Bad" training data are automatically weighted less than more significant data. Bad training data are data in which the good region and the bad region within an oily fruit are not very different and therefore a meaningful training model cannot be generated. By these methods, the differentiation, and therefore the parameter thereby erroneously defined as a reject, is reduced by a further factor of 5-10. Instead of ca. 5% false rejects in the sorting unit, this can be reduced to less than 1%. Thus, with the model trained in this manner, it is possible to predict whether the reject will fall into the desired range. Thus, the AI module can deliver significant parameters for the assessment of putrid oily fruit.

The AI used here does not require presegmentation of the spectra, but specific wavelengths are transferred to the neural network as preferred wavelengths. This means that the AI used can learn without any prior information. This has the advantage that with this method, there is more flexibility with different putrefaction products or fatty acid decomposition products. The trained AI autonomously calls upon the best range of values for an optimal selection result for the evaluation.

Quite generally, the AI module serves to construct a statistical model which is based on training data and is tested using test data in order, finally, to be applied to the data in the running product stream. The "algorithms which can be used" should in particular be understood to be supervised ML algorithms in which a training data set trains a model which is applied to further evaluation data in order to compute a classification. The strategies for training such models include Deep Learning (artificial neural nets), wherein several layers of artificial neurons link the input variables (feature vector) to the output variables (classification, regression, etc). Similarly, in addition, many other Machine Learning Methods, Random Forest Algorithms (randomised decision trees) or Support Vector Machines (estimation by means of support vectors in the vector space of the feature vectors) may be used, in particular in order to limit computer time.

A computer program product in accordance with the invention comprises program commands which are configured to execute at least one method as defined above. The computer program product may comprise command data, computed data and parameters, as described above.

A computer-readable medium in accordance with the invention comprises at least one computer program product which, when executed by at least one processing unit, enables the latter to carry out at least one of the aforementioned methods. The computer-readable medium may comprise control data, measurement data, computed data, measured values and parameters, as described above.

The method in accordance with the invention and the device in accordance with the invention as well as preferred and alternative exemplary embodiments will now be described in more detail with the aid of the figures.

Further advantages, features and details of the invention will become apparent from the description below in which exemplary embodiments of the invention are described with reference to the drawings.

The list of reference symbols along with the technical content of the patent claims and the figures form part of the disclosure. The figures are described coherently and comprehensively. Identical reference symbols indicate identical components; reference symbols with different indices indicate components with identical or similar functions.

The invention is described in more detail by means of the figures below with the aid of exemplary embodiments. The list of reference symbols forms a part of the disclosure.

Positional information such as "top", "bottom", "right" or "left" should be respectively understood to refer to the appropriate views and should not be understood to be limiting.

Although the invention has been represented by means of the figures and the associated description and is described in detail, this representation and this detailed description should be understood to be illustrative and by way of example, and does not limit the invention. It should be understood that the person skilled in the art could make changes and variations without departing from the scope of the claims below. In particular, the invention includes embodiments with any combination of features which have been mentioned or shown herein in respect of different aspects.

The invention also encompasses individual features in the figures, even if they are shown in connection with other features and/or are not mentioned here. Furthermore, the expression "comprise" and derivations thereof does not exclude other elements or steps. In addition, the indefinite article "a" or "an" and derivations thereof does not exclude a plurality. The functions of several features defined in the claims may be fulfilled by one unit. The terms "substantially", "approximately", "about" and the like in connection with a property or a value in particular also define exactly the property or exactly the value. All of the reference symbols in the claims should be understood not to limit the scope of the claims. Terms such as "first" or "second" serve merely to distinguish them from subsequent nouns and in all cases define a sequence or value of the subsequent nouns.

DESCRIPTION OF THE FIGURES

The figures are described coherently and comprehensively. Identical reference symbols refer to identical components. In the figures.

EMBODIMENT OF THE INVENTION

Figure 1:
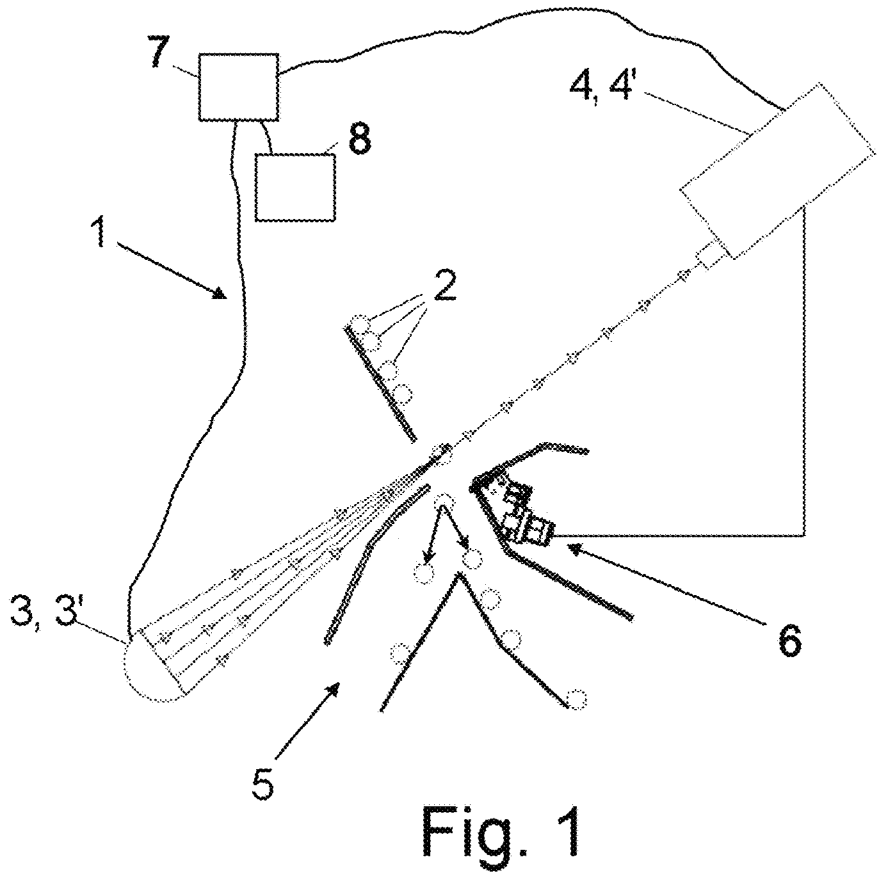
FIG. 1: shows a device for determining whether an oily fruit, a nut, in particular a hazelnut, or a seed is putrid.
Figure 3:
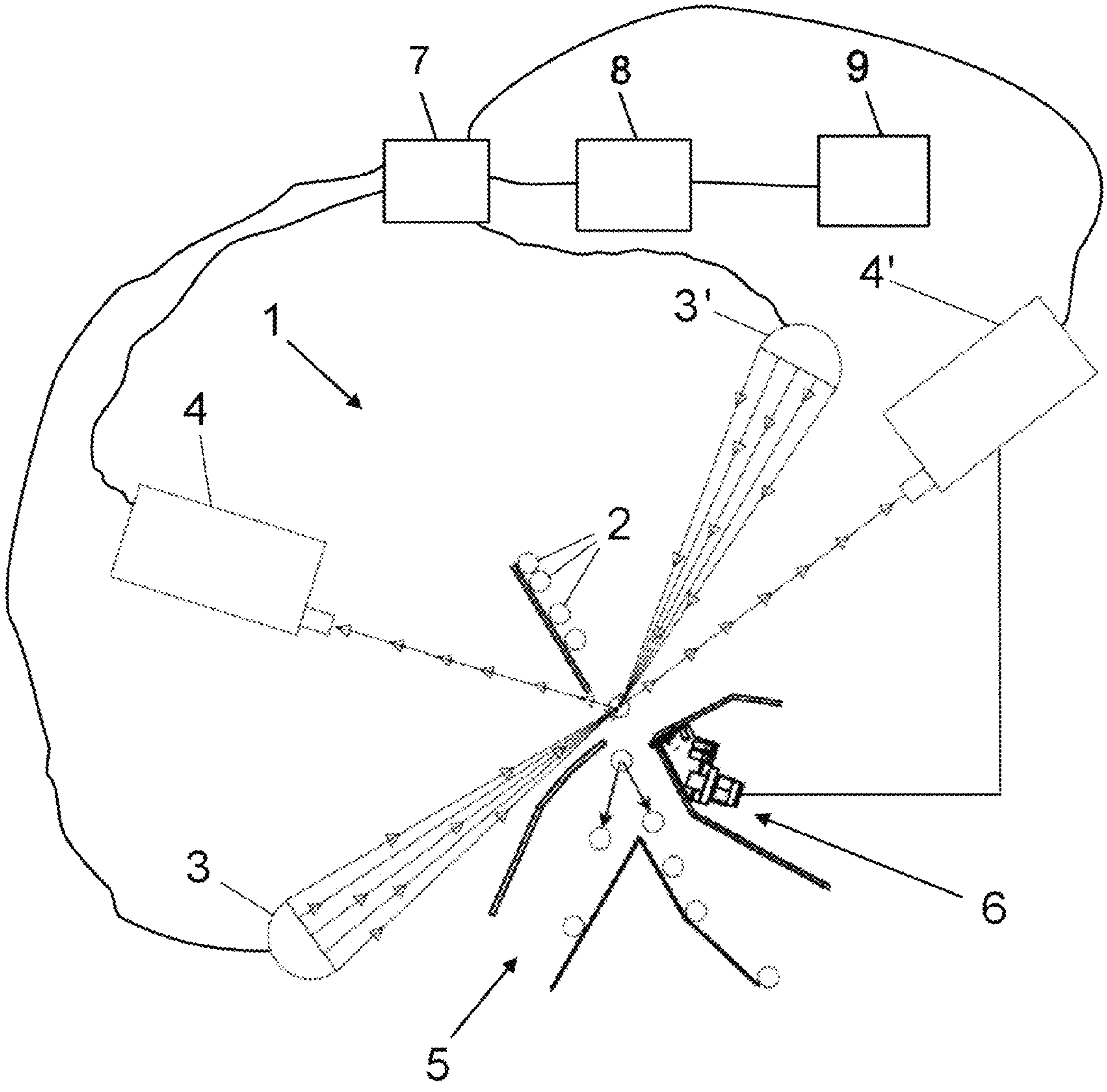
FIG. 3: shows a further alternative variational embodiment of the device in accordance with the invention.

FIG. 1 shows a device 1 in accordance with the invention for determining whether an oily fruit, a nut, in particular a hazelnut 2, or a seed is putrid, which is configured to execute a method in accordance with the invention, in a preferred embodiment. The device 1 in accordance with the invention comprises a calibrating light source 3, a detecting light source 3', a calibrating photosensor 4 and a detecting photosensor 4'. In the variational embodiment shown in FIG. 1, the calibrating photosensor 4 and the detecting photosensor 4' are configured as a common photosensor but, as can be seen in FIG. 3, they may also be separate photosensors. The method in accordance with the invention for determining whether an oily fruit, a nut, in particular a hazelnut 2, or a seed is putrid comprises a series of calibration steps and a series of detection steps. The calibration steps of the method in accordance with the invention comprise irradiating a sample of the oily fruit, the nut, in particular the hazelnut 2, or the seed with the calibrating light source 3. The light reflected and/or transmitted from the sample is then projected onto the calibrating photosensor 4, whereupon the calibrating photosensor 4 acquires an absorption or reflection spectrum in a wavelength range of 300-2500 nm, preferably 900-1700 nm. In addition, the calibration steps comprise determining a content of at least one fatty acid decomposition product in the sample, determining a degree of putrescence with the aid of the content of the at least one fatty acid decomposition product in the sample, and associating at least one characteristic wavelength or at least one characteristic wavelength range of the acquired absorption or reflection spectrum of the sample with the degree of putrescence. In the method in accordance with the invention, these preceding steps are repeated for a representative number of samples and a correlation function between the degree of putrescence and the associated wavelengths or wavelength ranges of the acquired absorption or reflection spectra is formed. The process of putrefaction of a hazelnut, for example, is linked to the formation of or to the decomposition of fatty acids. By means of the calibration steps, the method in accordance with the invention enables the content of at least one fatty acid decomposition product in the sample to be linked to a degree of putrescence, which allows the quality of the oily fruit, the nut, in particular hazelnut 2, or the seed to be evaluated. In addition, a characteristic wavelength or at least one characteristic wavelength range of the acquired absorption or reflection spectrum of the sample is associated with this degree of putrescence, which enables the degree of putrescence to be deduced from the absorption or reflection spectrum. Repetition for a representative number of samples means that a correlation function, for example, is formed, whereupon a direct conclusion as to the degree of putrescence is provided via the correlation function by means of an evaluation of the absorption or reflection spectrum. A conventional oily fruit, a nut, in particular a hazelnut 2, or a seed may be used as the sample. The device 1 comprises a control device 7 which controls at least one component from the group: calibrating photosensor, detecting photosensor, calibrating light source and detecting light source, so that at least one method described above can proceed automatically and reproducibly. The control device 7 controls the sorting unit 5. Here, the control device 7 has control data which controls the sorting unit 5. The device 1 comprises a processing unit 8 which evaluates spectral data in order to carry out a classification of the oily fruit. The spectral data may be measured data and may be used to generate control data for the control device 7.

This correlation function may then be used in the context of the detection steps of the method in accordance with the invention. These detection steps comprise irradiating an oily fruit, a nut, in particular a hazelnut 2, or a seed with the detecting light source 3'. The same light source may be used as both the calibrating light source 3 as well as the detecting light source 3', which is why the device 1 in accordance with the invention depicted in FIG. 1 is provided with only one light source.

In an alternative or additional embodiment, an index table or a value table may be used, wherein a direct conclusion regarding the degree of putrescence is drawn via the index table or the value table by means of an evaluation of the absorption or reflection spectrum.

Figure 2:
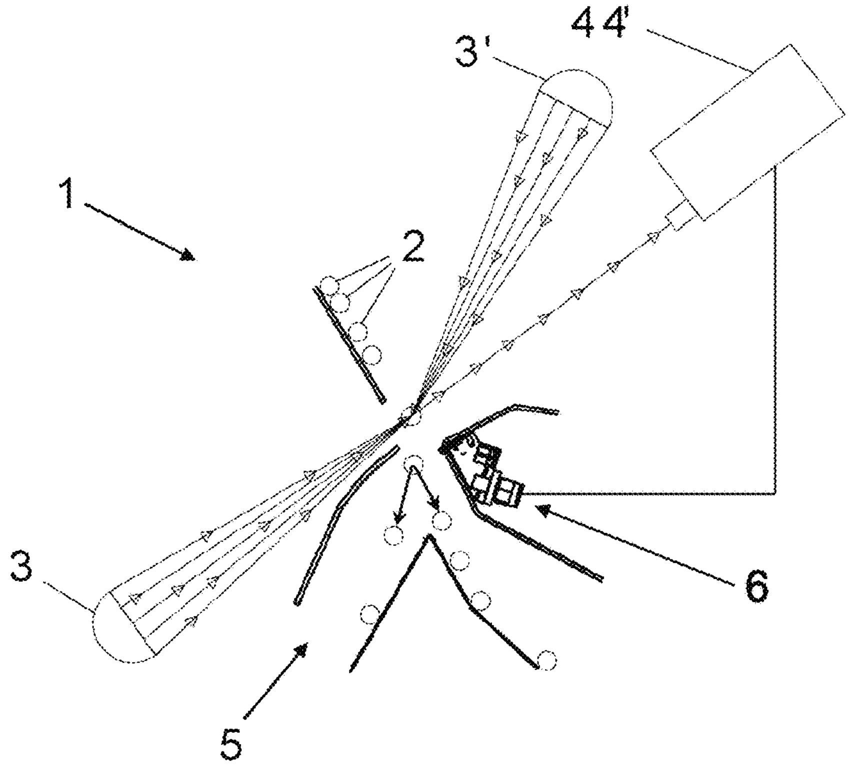
FIG. 2: shows an alternative variational embodiment of the device in accordance with the invention.

In accordance with the variational embodiment of the device 1 in accordance with the invention shown in FIG. 2, separate light sources may also be used as the calibrating light source 3 and as the detecting light source 3'. In accordance with the variational embodiment shown in FIG. 3, separate light sources are used as the calibrating light source 3 and as the detecting light source 3', and separate photosensors are used as the calibrating photosensor 4 and as the detecting photosensor 4'. The detection steps furthermore comprise projecting the light reflected and/or transmitted from the oily fruit, the nut, in particular the hazelnut 2, or the seed onto the detecting photosensor 4'. As explained with respect to the calibrating light source 3 and the detecting light source 3', a common sensor may also be used as the calibrating photosensor 4 and as the detecting photosensor 4'. This results in a reduction in the complexity of the device 1 in accordance with the invention. The device 1 in accordance with FIG. 2 also comprises a processing unit and control device (not shown), as described above.

In accordance with the variational embodiment of the device 1 in accordance with the invention shown in FIG. 3, different sensors may also be used as the calibrating photosensor 4 and as the detecting photosensor 4'. In accordance with this variational embodiment, both the detecting photosensor 4' as well as the calibrating photosensor 4 may operate in reflection. This means that light reflected from the sample is projected onto the calibrating photosensor 4 and light reflected from the seed 2 is projected onto the detecting photosensor 4'. As can be seen in FIGS. 1 and 2, the calibrating photosensor 4 and/or the detecting photosensor 4' may, however, also operate in transmission, wherein light transmitted from the sample is projected onto the calibrating photosensor 4 and/or the light transmitted from the seed 2 is projected onto the detecting photosensor 4'. In the context of the invention, the term "an oily fruit, a nut, in particular a hazelnut 2, or a seed" should be understood to mean both a roasted as well as an unroasted oily fruit, nut, in particular hazelnut, or seed.

In the context of the detection steps, in addition, the acquisition of absorption or reflection spectra is carried out in a wavelength range of 300-2500 nm, preferably 900-1700 nm, via the detecting photosensor 4'. The detecting photosensor 4' of the device 1 in accordance with the invention for carrying out the method in accordance with the invention has a plurality of pixels and each acquires one absorption or reflection spectrum per pixel. Next, a degree of putrescence is associated with each pixel of the detecting photosensor 4' by using the correlation function on the absorption or reflection spectra acquired by the pixels of the detecting photosensor 4'. Furthermore, a classification of the oily fruit, the nut, in particular the hazelnut 2, or the seed as putrid is made when at least a specific number of pixels exhibit a degree of putrescence which exceeds a first threshold value and/or when a degree of putrescence associated with at least one pixel exceeds a second threshold value. The device 1 in accordance with FIG. 3 also comprises a processing unit 8 and a control device 7 as well as an AI module 9, wherein the AI module 9 may also be present in the devices 1 of FIG. 2 or FIG. 3. The AI module is linked to the processing unit or is integrated into the processing unit. With the aid of the AI module, the difference, and therefore a parameter defined as what is known as an erroneous rejection, can be further reduced by a factor of 5-10. Instead of ca. 5% false rejections in the sorting unit 5, this can be reduced to less than 1%.

The method in accordance with the invention enables the putrescence of the oily fruit, the nut, in particular the hazelnut 2, or the seed to be determined with the aid of a spatially resolved determination of the degree of putrescence. In addition, by means of the first threshold value and the second threshold value, a non-homogeneous distribution of the fatty acid decomposition products in the oily fruit, the nut, in particular the hazelnut 2, or the seed can be incorporated into the evaluation of putrescence. By means of this, an improved distinction between a non-putrid hazelnut 2 and a putrid hazelnut 2, for example, can be made.

It is known that the process of putrefaction in a hazelnut, for example, is linked to the formation or to the decomposition of fatty acids. The standard reference analysis for the determination of fatty acids or their volatile decomposition products is a chromatographic determination by means of gas chromatography, also termed GC, and subsequent mass spectrometry. These invasive methods, however, can only identify either a homogenized mixed sample or the content of individual hazelnuts, but cannot selectively detect individual hazelnuts and reject in real time. FTIR analysis may also be mentioned here, as a non-invasive standard laboratory method. Based on an interferogram of the sample surface or of the homogenized sample, in this, a spectrum is computed by means of Fourier transformation. However, compared with the method in accordance with the invention, this method is also not suitable for sorting large mass flows such as 6 t/h, for example. During harvesting, but at the latest in the handling process, large quantities now have to be sorted in a manner such that a risk to health is eliminated and alterations to the flavour are avoided as far as possible. Even before further processing is carried out, the method in accordance with the invention enables oily fruits, nuts, in particular hazelnuts 2, or seeds for which the flavour has changed or which are toxicogenic or putrid to be detected in an automated manner and at high throughput rates.

During the hazelnut harvest, but at the latest in the handling process, the large quantities of hazelnuts 2 have to be sorted in a manner such that a risk to health is eliminated and alterations to the flavour are avoided as far as possible. Even before the hazelnuts are processed further, for example into chocolates or snacks, flavour-altering, toxicogenic or putrid hazelnuts 2 ought to be eliminated automatically at high throughput rates.

Because the flavour-altering substances such as free fatty acids and their decomposition products are distributed in a spatially non-homogeneous manner, for example in a hazelnut 2, in the method in accordance with the invention, the chemical content of homogenized samples are examined in the laboratory or measuring laboratory using analytical methods available in the laboratory such as gas chromatography or FTIR and with the aid of a statistically large quantity, and the determined concentration is correlated with the corresponding hyperspectral information. The detecting photosensor 4' can now be calibrated with the determined correlation between spectral response, such as wavelength and/or amplitude, for example, and the substance concentrations. In the case of a putrid hazelnut 2, there are changes in the free fatty acids. It has also been shown that the chemical changes inside a hazelnut 2, for example, correlate with the measurement on the surface. This is also the case for oily fruit, nuts or seeds. The method in accordance with the invention is particularly effective for oily fruit, nuts or seeds in which the seed skin is disposed in the optical path.

The solution in accordance with the invention consists of looking for fatty acid decomposition products in the spectral range used. In this regard, the model is preferably not limited to one chemical substance, but preferably to five main components which exhibit the largest differences in concentration between good and putrid oily fruits, nuts, in particular hazelnuts 2, or seeds. This means that in the crucial spectral range, with the aid of the measured values from several substances, from the absolute amplitudes in the spectrum, the quantitative degree of the flavour-altering substances can automatically be deduced. In accordance with the invention, the measured value is then defined as the degree of putrescence, for example in a range of 0-100%. Next, with the aid of the first threshold value and the second threshold value, sorting may be carried out, for example in a sorting unit.

Preferably, the association of the at least one characteristic wavelength or of the at least one characteristic wavelength range of the acquired absorption or reflection spectrum of the sample with the degree of putrescence in the context of the method in accordance with the invention is carried out by means of at least a mean, a bandwidth or individual frequency bands of the acquired absorption or reflection spectra. This means that for specific fatty acid decomposition products, representative wavelengths or wavelength ranges in the absorption or reflection spectrum can be called upon in order to determine the degree of putrescence. Furthermore, the acquisition of the absorption or reflection spectra is carried out by the calibrating photosensor 4 and/or the detecting photosensor 4', preferably by means of hyperspectral acquisition. Consequently, the calibrating photosensor 4 and/or the detecting photosensor 4' of the device 1 in accordance with the invention is preferably configured as a hyperspectral camera or as two separate hyperspectral cameras. Hyperspectral cameras enable the device 1 in accordance with the invention or the method in accordance with the invention to be used in modern sorting units in the foodstuffs domain. In contrast to normal colour cameras, these not only detect in the visible light range, but also in additional spectral ranges, for example in the infrared range. Because the recordings in the infrared region provide information regarding the chemical properties on the surface of the product by means of Chemical Imaging Technology, they are highly suitable for representing the quality of foodstuffs and detecting poor quality, defects or contamination which are hidden to the human eye. In contrast to analytical methods in the laboratory or measuring laboratory, with the aid of automatization technology, these photographic analytical methods are suitable for inspecting high material throughputs of foodstuffs and of high-speed, real-time separation in sorting units.

In order to determine the content of the at least one fatty acid decomposition product in the sample, preferably, gas chromatography and adjoining mass spectrometric analysis is carried out. This enables a precise determination of the content of the fatty acid decomposition product in the sample to be made.

As can be seen in FIG. 1 and in FIG. 2, the device 1 in accordance with the invention preferably comprises a sorting unit 5. This is configured to reject an oily fruit, a nut, in particular a hazelnut 2, or a seed from a product stream when the oily fruit, the nut, in particular the hazelnut 2, or the seed is classified as putrid. The sorting unit 5 here may, for example, comprise a pneumatic deflecting unit 6, which is linked to the detecting photosensor 4'. The pneumatic deflecting unit separates oily fruit, nuts, in particular hazelnuts 2, or seeds which have been classified as putrid out of a substantially continuous stream of product.

The method in accordance with the invention comprises the sensory acquisition of hazelnut kernels, or in general oily fruit, nuts or seeds, acquired in reflectance or transmittance, in a wavelength range of 300-2500 nm or a sub-range thereof, preferably by means of a hyperspectral or multispectral camera. The spatially resolved spectral data obtained in this manner are evaluated with a processing unit 8 such as a PC, an embedded system with FPGA, CPU or GPU, in a manner such that they are correlated in a training mode with measured values originating from a reference laboratory regarding the chemical component determination in hazelnuts, for example, obtained using GO, for example. The correlation obtained for training, i.e. that spectral information which can be brought together with the information in the reference data set, is then used in an operating mode which is characterized by the detection steps in order to associate an appropriate measured value for the putrescence with newly recorded spectra. Thus, every pixel in the camera's field of view corresponds to a reference value based on the calibration by the determined correlation between spectral data and the measuring laboratory.

Any suitable statistical method from the field of multivariate regression analysis may be used as the method for extracting the appropriate correlation information and which, for example, correlates the variance in the spectral data set with that in the measuring laboratory data set. Non-limiting examples of such methods are Principal Component Regression (PCR), Partial Least Squares Regression (PLSR), Multiple Linear Regression (MLR), Multivariate Curve Resolution (MCR), soft independent modelling of class analogy (SIMCA), Support Vector Regression (SVR), regression using artificial neural networks, decision trees, and/or random forests.

On the basis of the spatially resolved optical measurement of the surfaces of oily fruit, nuts, in particular hazelnuts 2, or seeds collected in this manner, the definition of the first threshold value and of the second threshold value can be determined as to whether, for example, an inspected almond might be putrid or counted as a good product. The first threshold value defines how many putrescence pixels per object, for example the almond or a hazelnut 2, above which the object is to be categorised as putrid. The second threshold value defines the point from which a pixel value for the camera field of view is to be counted as putrid.

Figure 4:
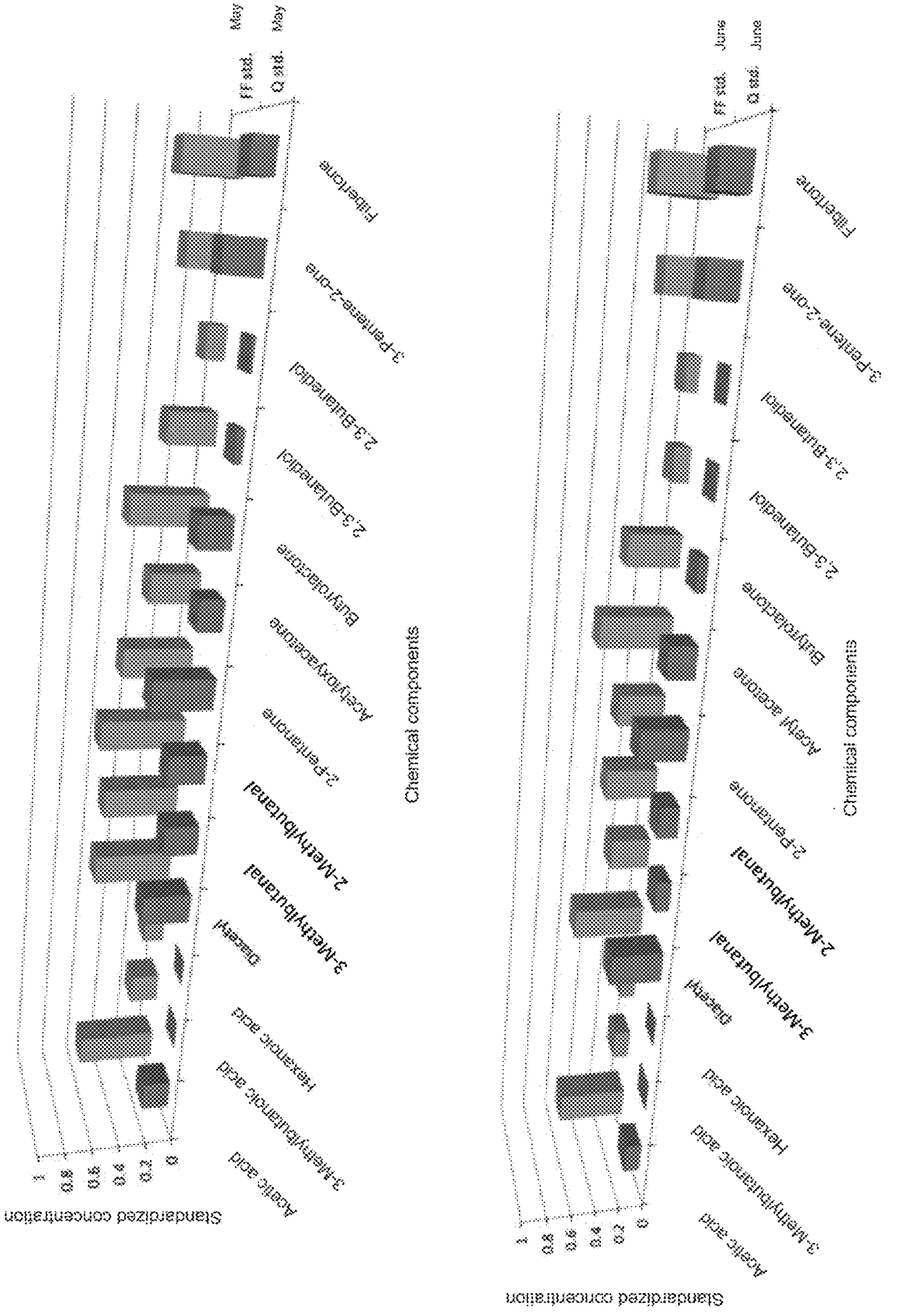
FIG. 4 shows a standardized concentration of fatty acid decomposition products for putrid hazelnuts and those fatty acid decomposition products with the greatest differences between a putrid hazelnut (Q) and a non-putrid hazelnut (FF).

FIG. 4 shows an exemplary evaluation of fatty acid decomposition products in the case of putrid hazelnuts 2 in the context of a selection of those fatty acid decomposition products with the greatest differences between a putrid hazelnut and a non-putrid hazelnut.

Preferably, butyrolactone, diacetyl, 2-methylbutanal, 3-methylbutanal, acetylacetone, filbertone and 2,3-butanediol are specified as fatty acid decomposition products in the context of the method in accordance with the invention. Putrescence is in particular due to butyrolactone, a cyclic ester of hydroxycarbonic acids. In particular, the fatty acid decomposition products of the sample can be identified by mass spectroscopic detection to establish chromatograms for a range of between 20 and 300 selected mass/charge ratios, preferably for at least a mass/charge ratio of 86 for butyrolactone, diacetyl, 2-methylbutanal, 3-methylbutanal and acetylacetone, 45 for 2,3-butanediol, and 69 for filbertone. The mass/charge ratio for acetic acid is typically 60.

The device 1 in accordance with the invention, which preferably comprises a sorting unit 5, as well as the method in accordance with the invention, have the following advantages in particular:

A high processing speed and decision-making reliability in the in-line sorting process, due to the evaluation of the correlation between the concentration of at least two fatty acid decomposition products and spectral response. Furthermore, a qualitative high off-line concentration determination based on the current status of off-line laboratory technology is obtained which can be used in-line in the sorting process.

In accordance with the invention, sorting of putrescence is not a bivalent variable such as putrid or not putrid, but is based on an analogue variable which is based on the amplitude at specific wavelengths or the mean of the amplitudes in a wavelength range and a spatial distribution in the hazelnut 2, for example, by surface measurement. Based on the detection of the spectral degree of putrescence, sorting can be carried out using high product quality criteria and precise setting of the sorting thresholds in the sorting unit.

LIST OF REFERENCE SYMBOLS

2 oily fruit, in particular hazelnut
3 calibrating light source
3' detecting light source
4 calibrating photosensor
4' detecting photosensor
5 sorting unit
6 deflecting unit
7 control device
8 processing unit
9 AI module

The invention claimed is:

1. A method for determining whether an oily fruit, a nut or a seed is putrid, comprising at least the following calibration steps:

a) irradiating a sample of an oily fruit, a nut or a seed with a calibrating light source, b) acquiring an absorption or reflection spectrum in a wavelength range of 300-2500 nm by means of a calibrating photosensor, c) associating at least one characteristic wavelength or at least one characteristic wavelength range of the acquired absorption or reflection spectrum of the sample with a degree of putrescence, and d) repeating the preceding steps for a representative number of samples and forming a correlation between the degree of putrescence and the associated wavelengths or wavelength ranges of the acquired absorption or reflection spectra, wherein the method then comprises the following detection steps:

e) irradiating an oily fruit, a nut or a seed with a detecting light source, f) acquiring absorption or reflection spectra in a wavelength range of 300-2500 nm by means of a detecting photosensor, wherein the detecting photosensor has a plurality of pixels and each acquires one absorption or reflection spectrum per pixel, g) associating a degree of putrescence with each pixel of the detecting photosensor by applying the correlation in accordance with step d) to the absorption or reflection spectra acquired from the pixels of the detecting photosensor, and h) classifying the oily fruit, the nut or the seed as putrid when at least a specific number of pixels have a degree of putrescence which exceeds a first threshold value and/or when a degree of putrescence associated with at least one pixel exceeds a second threshold value.

2. The method as claimed in claim 1, wherein a wavelength range of 900-1700 nm is used in step b).

3. The method as claimed in claim 1, wherein after step b), at least one degree of putrescence is determined with the aid of the content of at least one fatty acid decomposition product in the sample.

4. The method as claimed in claim 3, wherein the at least one fatty acid decomposition product comprises at least one component from the group:

butyrolactone, diacetyl, 2-methylbutanal, 3-methylbutanal, acetylacetone, filbertone or 2,3-butanediol.

5. The method as claimed claim 3, wherein the degree of putrescence is determined with the aid of the contents of at least two fatty acid decomposition products in the oily fruit.

6. The method as claimed in claim 3, wherein several components of the fatty acid decomposition products which have the largest difference in concentration between good and putrid oily fruits, nuts, or seeds are searched for.

7. The method as claimed in claim 1, wherein the correlation is at least one correlation function or at least one index table or a value table, or comprises at least one comparison of spectral information which comprises at least the degree of putrescence of the oily fruit and the wavelengths or wavelength ranges of the acquired absorption or reflection spectra associated therewith.

8. The method as claimed in claim 1, wherein a wavelength range of 900-1700 nm is used in step e).

9. The method as claimed in claim 1, wherein the calibrating photosensor is the detecting photosensor.

10. The method as claimed in claim 1, wherein one light source is used as the calibrating light source and as the detecting light source.

11. The method as claimed in claim 1, wherein the association of the at least one characteristic wavelength or of the at least one characteristic wavelength range of the acquired absorption or reflection spectrum of the sample with the degree of putrescence is carried out by means of at least one mean, a bandwidth or individual frequency bands of the acquired absorption or reflection spectrum.

12. The method as claimed in claim 1, wherein the acquisition of the absorption or reflection spectra is carried out by the calibrating photosensor and the detecting photosensor by means of hyperspectral acquisition and by means of a colour camera.

13. The method as claimed in claim 1, wherein the correlation in an operating mode which is characterized by the detection steps is used in order to associate a corresponding measured value for the degree of putrescence with newly recorded spectra.

14. The method as claimed in claim 1, wherein a reference value based on the calibration by means of a determined correlation between spectral data and a measuring laboratory corresponds to each pixel.

15. A device for determining whether an oily fruit, a nut or a seed is putrid, comprising the calibrating light source, the detecting light source, the calibrating photosensor and the detecting photosensor, wherein the device performs the method as claimed in claim 1.

16. The device as claimed in claim 15, wherein the device comprises a sorting unit, wherein the sorting unit is configured to reject an oily fruit, a nut or a seed from a product stream when the oily fruit, the nut or the seed is classified as putrid.

17. The device as claimed in claim 16, wherein the sorting unit operates at least with two adjustable threshold values, wherein a first adjustable threshold value comprises a substance quantity for a pixel and the second adjustable threshold value comprises a non-homogeneous distribution of the substance, in which for sorting, the second adjustable threshold value takes into consideration the number of pixels with the attribution: putrid.

18. The device as claimed in claim 15, wherein the device comprises a processing unit which evaluates spectral data.

19. The device as claimed in claim 18, wherein an AI module is present which is linked to the processing unit.

20. A computer program product comprising program commands that are executed by a computer to carry out the method as claimed in claim 1.

* * * * *